(12) United States Patent
Shanler

(10) Patent No.: US 7,666,362 B2
(45) Date of Patent: Feb. 23, 2010

(54) MICRO-PLATE AND LID FOR ROBOTIC HANDLING

(75) Inventor: Michael S. Shanler, Bedford, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 869 days.

(21) Appl. No.: 10/943,687

(22) Filed: Sep. 17, 2004

(65) Prior Publication Data

US 2005/0226787 A1  Oct. 13, 2005

Related U.S. Application Data

(60) Provisional application No. 60/557,977, filed on Mar. 31, 2004.

(51) Int. Cl.
*B01L 3/00* (2006.01)
(52) U.S. Cl. .................. 422/102; 422/99; 435/288.3; 435/288.4; 435/305.1; 435/305.2
(58) Field of Classification Search ............... 422/99, 422/102, 104; 435/288.3, 288.4, 305.1, 305.2, 435/305.3, 305.4
See application file for complete search history.

(56) References Cited

U.S. PATENT DOCUMENTS

| | | | | |
|---|---|---|---|---|
| 4,038,149 | A * | 7/1977 | Liner et al. | ............... 435/305.3 |
| 5,048,957 | A | 9/1991 | Berthold et al. | |
| 5,213,505 | A | 5/1993 | Laipply | |
| 5,358,871 | A | 10/1994 | Stevens et al. | |
| 5,650,323 | A | 7/1997 | Root | |
| 5,741,463 | A | 4/1998 | Sanadi et al. | |
| D411,308 | S | 6/1999 | Pandey et al. | |
| 5,910,287 | A | 6/1999 | Cassin et al. | |
| 5,939,024 | A | 8/1999 | Robertson | |
| 5,972,694 | A | 10/1999 | Mathus | |
| D420,743 | S | 2/2000 | Monks | |
| 6,054,325 | A * | 4/2000 | Kedar et al. | .................. 436/178 |
| 6,063,338 | A | 5/2000 | Pham et al. | |
| D428,157 | S | 7/2000 | Coassin et al. | |
| 6,171,780 | B1 | 1/2001 | Pham et al. | |
| 6,229,603 | B1 | 5/2001 | Coassin et al. | |
| 6,232,114 | B1 | 5/2001 | Coassin et al. | |
| 6,323,035 | B1 | 11/2001 | Kedar et al. | |
| 6,326,212 | B1 | 12/2001 | Aoki | |
| 6,340,589 | B1 | 1/2002 | Turner et al. | |
| 6,376,233 | B1 | 4/2002 | Wolf et al. | |
| 6,426,050 | B1 * | 7/2002 | Pham et al. | .................. 422/104 |
| 6,426,215 | B1 | 7/2002 | Sandell | |
| 6,486,401 | B1 | 11/2002 | Warhurst et al. | |
| D469,544 | S | 1/2003 | Lafond et al. | |
| 2002/0179590 | A1 | 12/2002 | Kwasnoski et al. | |

* cited by examiner

*Primary Examiner*—Lyle A Alexander
*Assistant Examiner*—Dwayne K Handy
(74) *Attorney, Agent, or Firm*—Hoffmann & Baron, LLP

(57) ABSTRACT

A well plate assembly includes a well plate with a base wall, a peripheral wall extending up from the base wall and spaced inwardly from the outer periphery of the base wall. A well array is formed on the base wall at locations inwardly from the peripheral wall. A lid is mounted on the peripheral wall of the well plate. The lid and the peripheral wall have areas that are indented from the outer periphery of the base wall to facilitate manipulation by robotic stacking equipment. The well plate and the lid further include substantially registered robotic gripper plates aligned with the outer periphery of the base wall to facilitate manipulation of the assembled well plate and lid by robotic grippers.

16 Claims, 6 Drawing Sheets

MICRO-PLATE AND LID FOR ROBOTIC HANDLING

RELATED APPLICATIONS

This application claims the benefit of U.S. Provisional Application No. 60,557,977 filed on Mar. 31, 2004 which is hereby incorporated by reference in its entirety.

BACKGROUND OF THE INVENTION

1. Field of the Invention

The invention relates to an assembly of a micro-plate and a lid that can be manipulated by robotic stackers and/or by robotic arms.

2. Description of the Related Art

Many laboratory procedures require analysis to be performed on chemicals or biological specimens, such as tissue cultured cells, proteins and enzymes. The specimen may be deposited in a liquid growth medium or buffer. An analysis then is performed after a specified time which will vary depending upon the nature of the biological specimen and the type of analysis that is to be performed.

The chemical or biological specimen often is deposited in a micro-plate. The plate may be moved from a first location where the specimen is deposited to a second location where the specimen is permitted to grow or otherwise develop over a specified time. The specimen then will be moved to another location for analysis.

The typical micro-plate for performing the above-described laboratory analysis is rectangular with a bottom wall, upstanding sidewalls and an open top. A lid may be mounted to the open top of the sidewalls to control evaporation. The footprint defined by the bottom wall of the plate generally is one of several standard sizes dimensioned to accommodate robotic handling equipment in a laboratory. Other characteristics of the plates, however, vary considerably from one manufacturer to another and from one type of analysis to another. One significant difference relates to the number of biological specimens that can be accommodated in the plate. For example, some plates define a single large reservoir in which tissue cultures may grow. Other laboratory analysis can be carried out with low volume assays. Thus, a single plate can accommodate a plurality of wells into which liquid and/or tissue cultures can be deposited. The plurality of wells typically are arranged in a rectangular matrix with formats that conform to standard formats for pipettes. For example, some standardized micro-plates include 2, 4, 8, 24, 96, 384, 1,536, 3456, or 4,080 wells.

A micro-plate with an appropriate number of wells can be molded unitarily in a dedicated mold for the particular number of wells. However, some micro-plates are formed from plural parts that are assembled together. For example, the micro-plate may include a unitary frame and a separate unitary well array with a pattern of wells. The well array with an appropriate number of wells is assembled to the standard frame.

Micro-plates often are stored in stacked arrays in the laboratory while the tissue or other biological material in the wells is permitted to grow. The micro-plates then are moved from the stacked array robotically and are transferred to appropriate work stations for analysis. There are two different approaches for robotically transferring the micro-plates from the stacked array to the work station for analysis. One option employs robotic gripping devices with grippers or fingers that grab opposite sides of the plates for transfer to a work station. Robotic grippers generally function to grab the top plate in a stacked array. The robotic grippers then lift the plate from the top of the stack and transfer the plate to the appropriate work station. Other laboratory devices stack the micro-plates in a magazine that permits the plates to be removed sequentially from the bottom of the stacked array. More particularly, the stack of plates may rest on two sets of solenoid controlled pins or levers that can retract and extend. Retraction of the pins releases the bottom plate in the array. The pins then extend to catch beneath the next plate, while the remaining stack of plates indexes down one position. The bottom plate is released onto an elevator lift that rises up from a location beneath the stacked array to engage the plate and to keep the plate aligned horizontally, thereby avoiding spills. The plate then is lowered by the elevator lift onto a shuttle that moves the plate to the appropriate work station.

Robotic grippers must have specialized features for contacting the plate. These features may include gripper pads, gripper points, gripper fingers or a serrated edge. These gripping features typically require smooth uninterrupted flat surfaces on the plate and/or the lid for proper engagement. Many plates can be handled efficiently by robotic grippers when the plate is stored independently of a lid. However, robotic grippers are likely to encounter gripping difficulties when the plate is being manipulated with the lid in place. More particularly, the known plate/lid assemblies are not configured for simultaneously gripping the lid and the plate in a manner that will hold the plate and lid in their assembled condition. There is the potential that the robotic gripper will grip only the lid or that the robotic gripper will grip portions of the lid below the top-most plate in a stacked array. Thus, many plates are stacked without lids to facilitate manipulation by robotic grippers. However, the absence of a lid significantly increases evaporation rates.

Robotic stackers that remove plates sequentially from a stacked array also encounter problems with lids. More specifically, the stacker is not well suited to distinguishing between a plate and a lid. Thus, the stacker may drop just the plate from the magazine, while retaining the lid for the dropped plate. The next cycle, then will drop the retained lid.

In view of the above, it is an object of the subject invention to provide a plate and lid assembly that is well suited to robotic handling by both robotic grippers and stackers.

It is another object of the subject invention to provide a micro-plate molding method for efficiently producing plates with a plurality of different well arrays.

A further object of the subject invention is to provide a plate and lid assembly that resists evaporation and facilitates robotic manipulation.

SUMMARY OF THE INVENTION

The invention is a well plate assembly that is suited for automated handling by robotic equipment. The assembly includes a well plate and a lid. The well plate includes a substantially rectangular base wall with opposite end edges and opposite side edges extending between the end edges. The end edges and the side edges of the base wall define a footprint conforming to a standard specified footprint for the laboratory equipment with which the assembly is to be used. The well plate further includes a well array that may be formed unitarily with the base wall. The well array includes at least one open-topped well for receiving liquid that will be subject to analysis in the laboratory. In many embodiments, the well array will include a rectangular matrix of open-topped wells, with the particular pattern of wells in the matrix conforming to the laboratory equipment with which the plate assembly is used. The well plate preferably includes a peripheral wall with opposite end walls spaced inwardly from the end edges of the base wall and opposite sidewalls spaced inwardly from the side edges of the base wall. The sidewalls meet the respective end walls at four corners. The end walls and/or the sidewalls preferably are formed with indentations for stacker compatibility. More particularly, the indentations are disposed to align with the solenoid indexing pins of the stacker.

The well plate may further include robotic gripper pads that project up from the side edges and/or the end edges of the bottom wall. The robotic gripper pads define relatively large outer peripheral areas that can be engaged by robotic grippers for lifting the well plate assembly from the top of a stacked array of well plate assemblies.

The lid of the well plate assembly includes a top wall and a peripheral frame. The top wall may include a substantially planar center panel that is recessed with respect to at least portions of the peripheral frame. The center panel may be dimensioned and configured for support on the top of the well array so that the center panel of the top wall of the lid closes the open tops of the wells. The peripheral frame of the top wall is configured to rest on top edges of the peripheral wall of the well plate. The lid further includes a peripheral skirt configured to nest with the peripheral wall of the well plate. Thus, the peripheral skirt of the lid is formed with indentations that will nest with the indentations on the peripheral wall of the well plate. Accordingly, the indentations in the peripheral skirt of the lid will align with the solenoid indexing pins of the stacker.

The lid of the well plate assembly may also include robotic gripper pads that register with the robotic gripper pads that project up from the bottom wall of the well plate. Thus, the outer surfaces of the robotic gripper pads on the lid cooperate with outer surfaces of the robotic gripper pads of the well plate to define regions that may be engaged by robotic grippers.

The subject invention also relates to a method for forming a well plate. The method includes injection molding the well plate with a first mold plate corresponding to the base wall of the well plate and a plurality of second mold plates corresponding to a plurality of different well arrays. Each of the plurality of second mold plates is configured to form one of the specified matrices of wells compatible with laboratory equipment. The method comprises selecting an appropriate second mold plate for use with the first mold plate to achieve the appropriate matrix of wells. The first and second mold plates then are secured in opposed relationship to one another and a resin is injected into the cavity defined between the first mold plate and the selected second mold plate.

DETAILED DESCRIPTION

Figure 1:
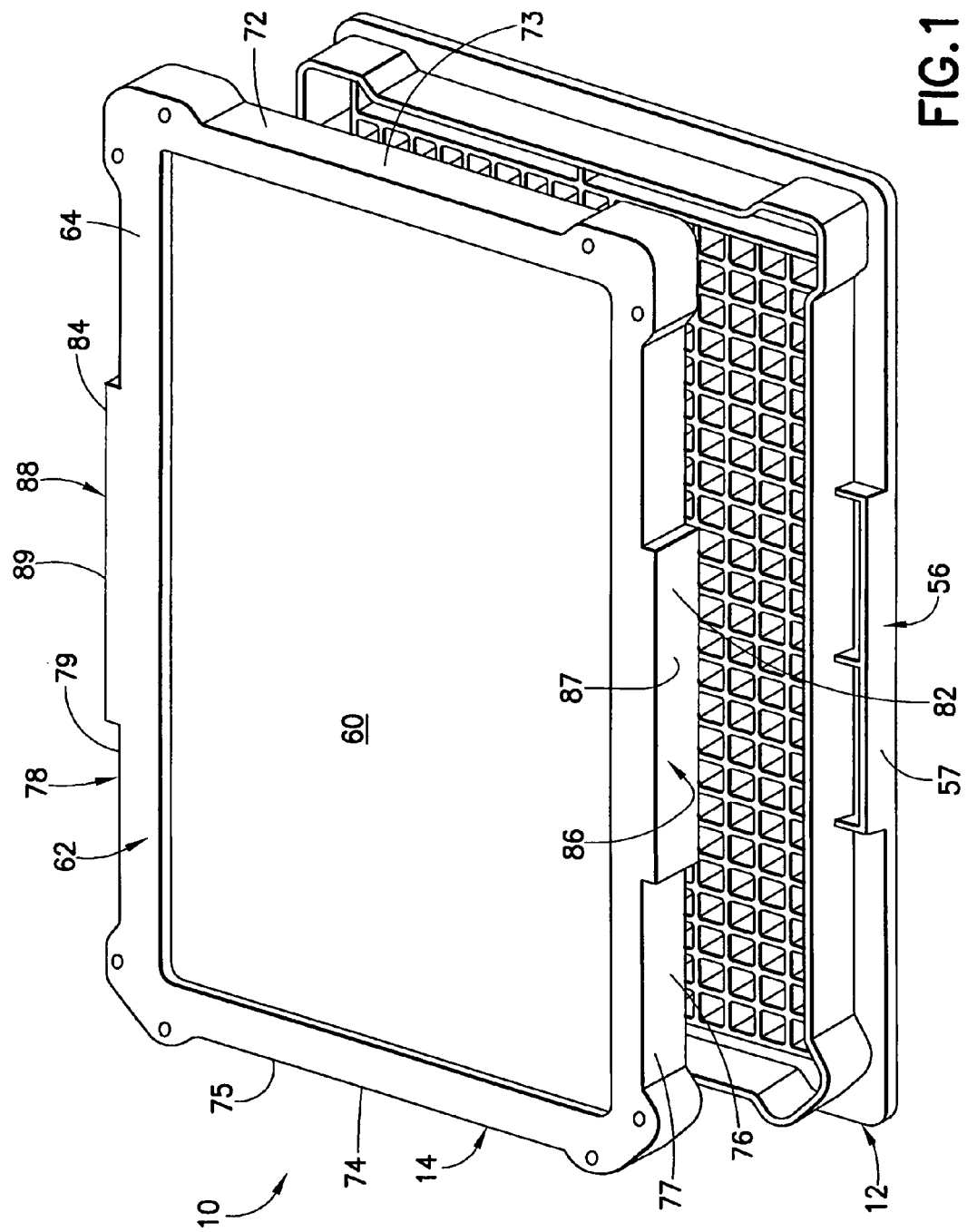
FIG. 1 is an exploded perspective view of a well plate and lid in accordance with the subject invention.
Figure 4:
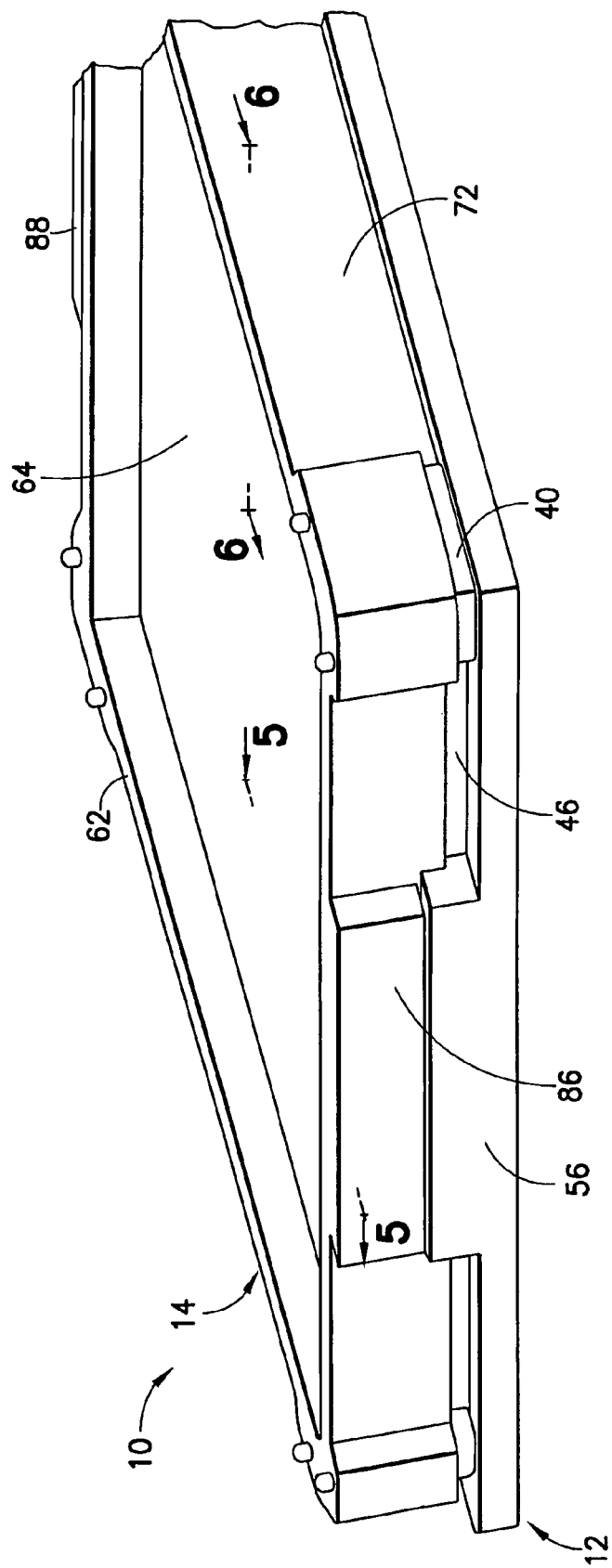
FIG. 4 is a prospective view of the well plate and lid in their assembled condition.
Figure 5:
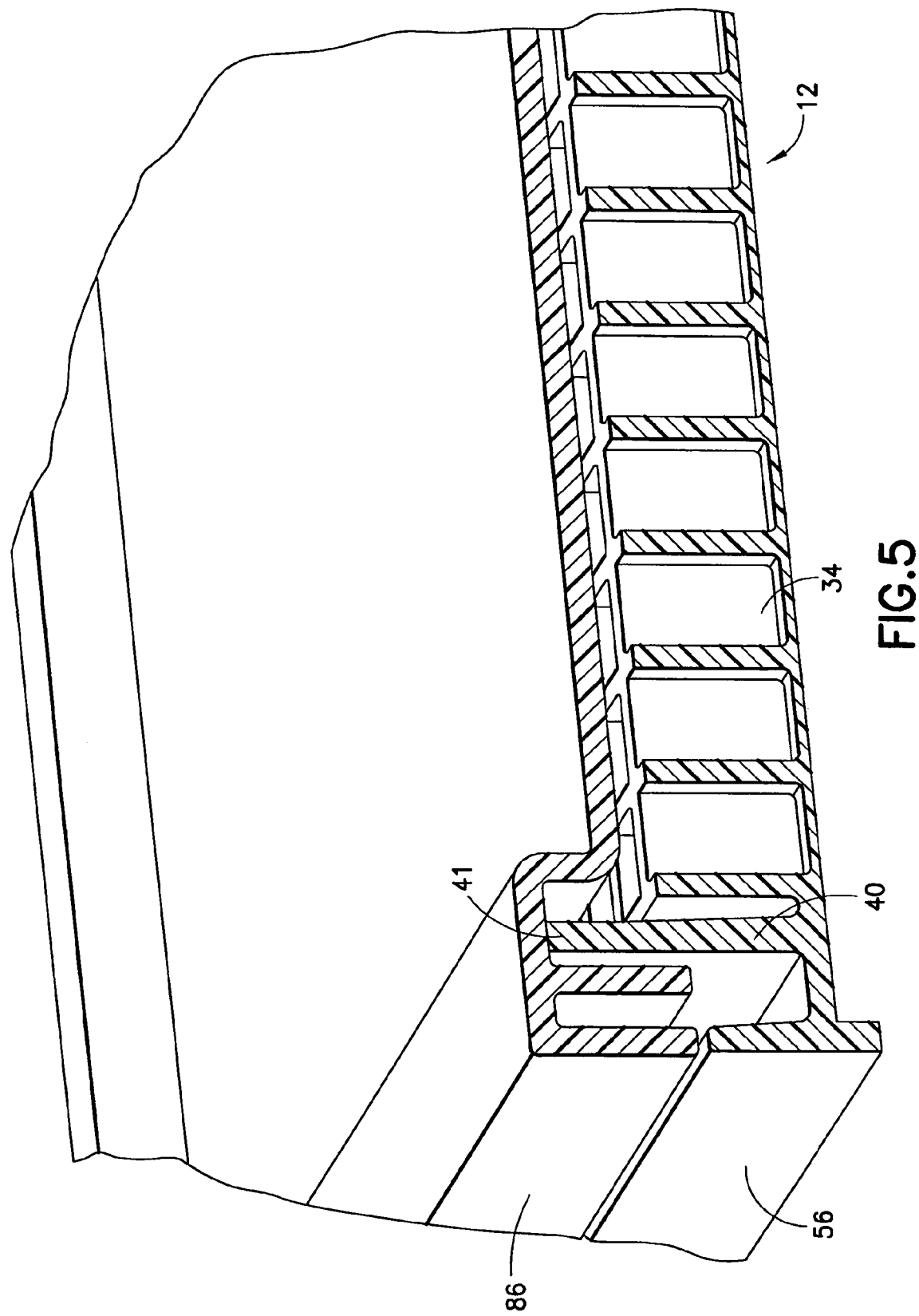
FIG. 5 is a cross-sectional view taken along line 5-5 in FIG. 4.
Figure 6:
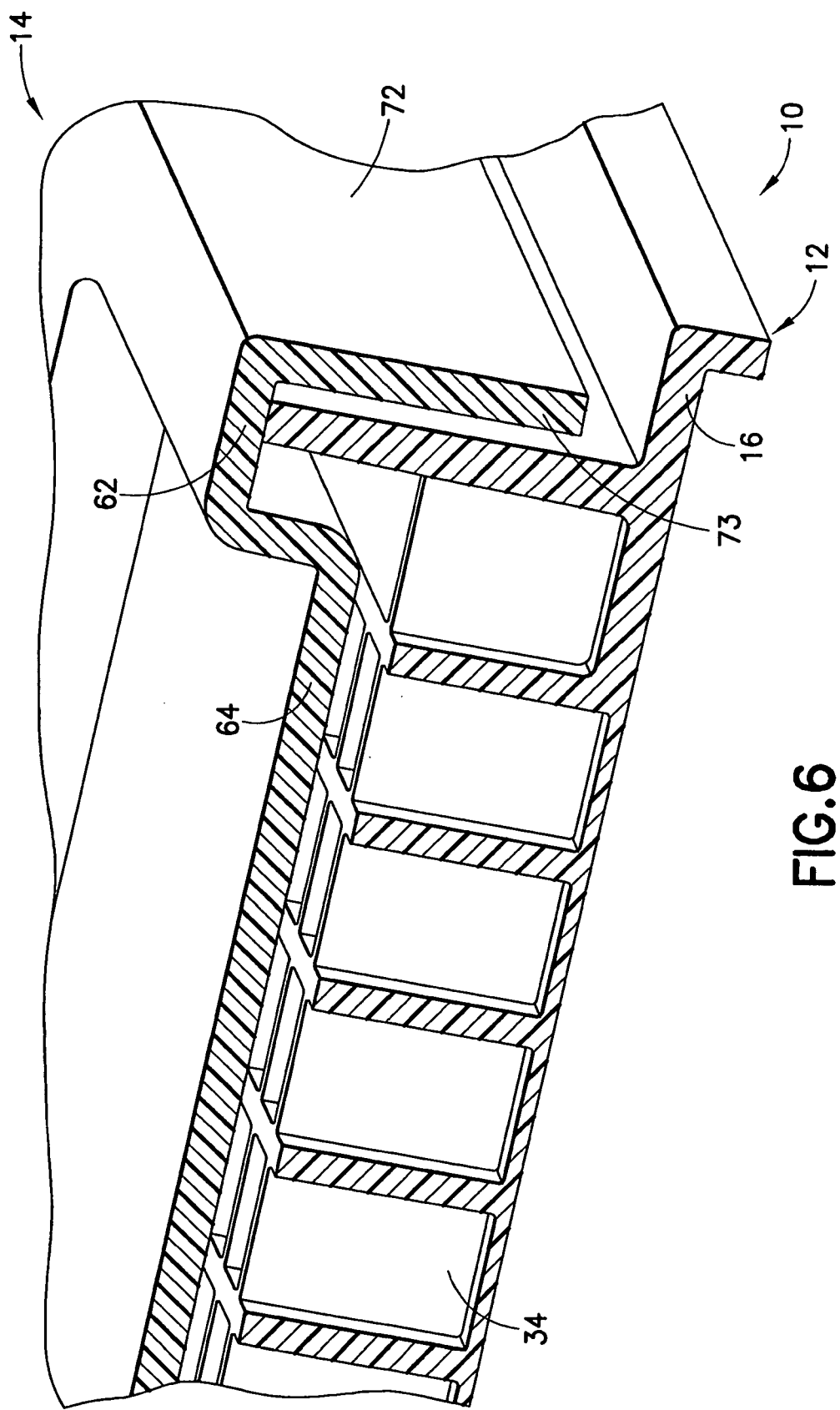
FIG. 6 is a cross-sectional view taken along line 6-6 in FIG. 4.

A plate assembly in accordance with the invention is identified generally by the numeral 10 in FIGS. 1 and 4-6. The plate assembly 10 includes a well plate 12 and a lid 14.

The well plate 12 is molded unitarily from a resin material such as polypropylene, polystyrene cyclic olfin, or polycarbonate. Well plate 12 includes a substantially planar base wall 16 and a downwardly depending skirt 20. Skirt 20 includes first and second substantially parallel ends 22 and 24 and first and second substantially parallel sides 26 and 28. Ends 22 and 24 are of substantially equal length and are substantially linear. Sides 26 and 28 also are of substantially equal length and are substantially linear. However, sides 26 and 28 are longer than ends 22 and 24. Thus, skirt 20 defines a substantially rectangular footprint for well plate 12. The dimensions of the footprint defined by skirt 20 of well plate 12 are selected in accordance with standardized dimensions for multi-wall plates and the laboratory equipment with which such plates are used.

Well plate 12 is characterized further by a well array 30 formed unitarily with base wall 16. Well array 30 is generally rectangular and is spaced inwardly from first and second ends 22 and 24 and first and second sides 26 and 28 of skirt 20. Well array 30 includes a substantially planar top surface 32 aligned substantially parallel to base wall 16. Top surface 32 of well array 30 is characterized by a plurality of upwardly open wells 34 that extend down toward base wall 16. Wells 34 are arranged in well array 30 to define a substantially rectangular matrix. The number of wells 34 may vary depending upon the types of tests that will be carried out with plate assembly 10 and the types of laboratory equipment that will be employed to carry out such tests. However, the matrix of wells 34 typically will conform to a pattern of pipettes or other sample accommodating equipment. Thus, well array 30 may have 1; 2; 4; 8; 24; 96; 384; 1,536; 3,456; 4,080 or some other standardized number of wells 34.

Figure 2:
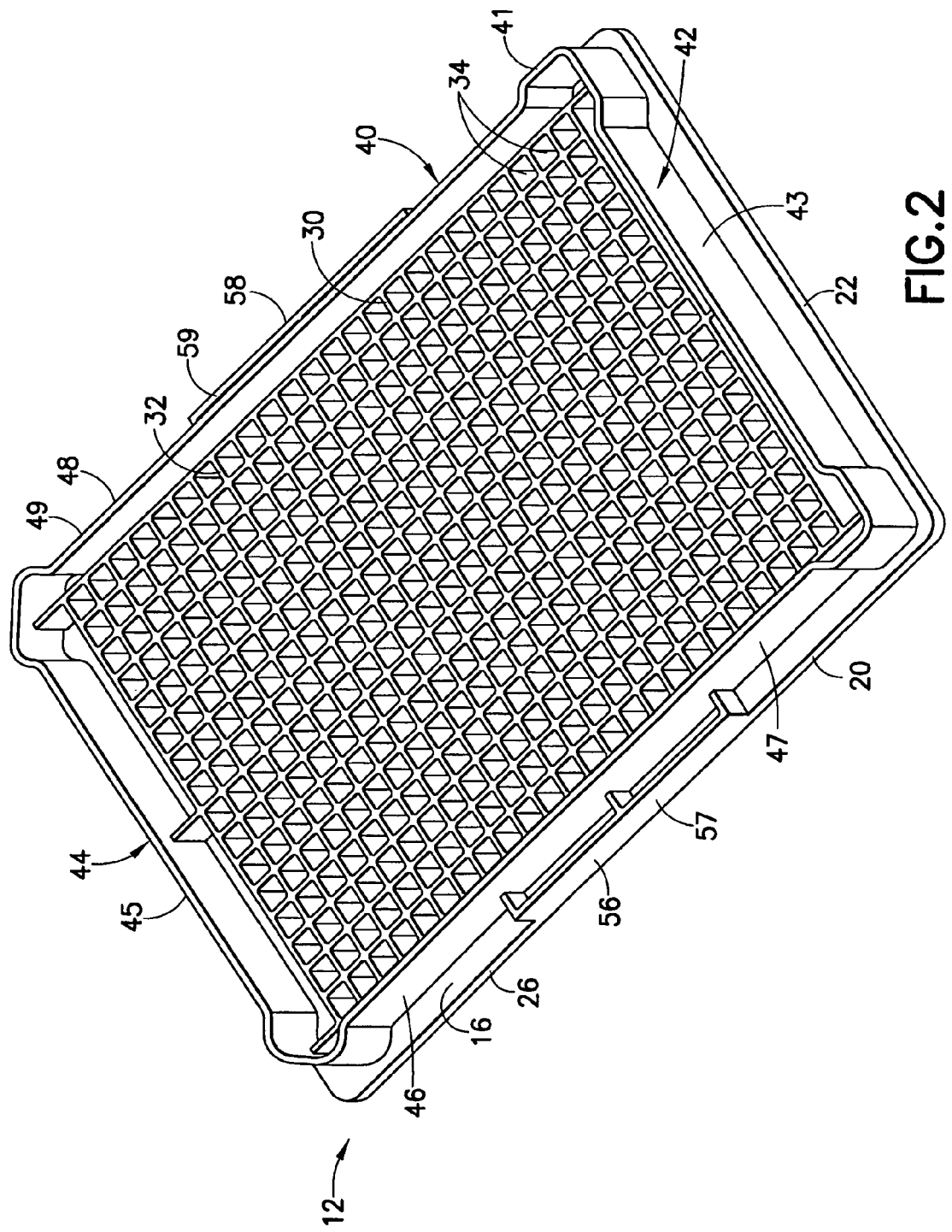
FIG. 2 is a perspective view of the well plate.
Figure 3:
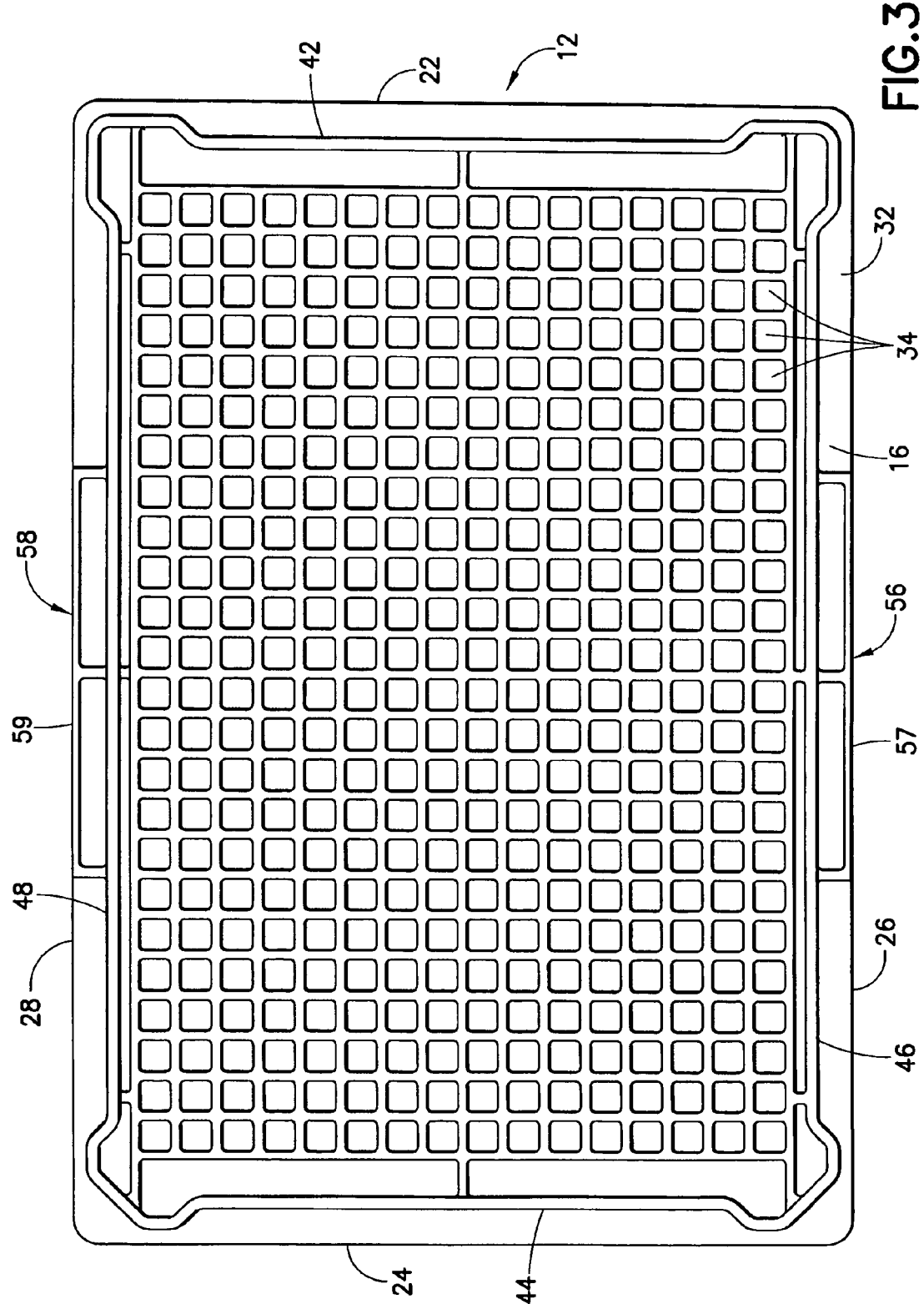
FIG. 3 is a top plan view of the well plate.

Well plate 12 further includes an outer peripheral sidewall 40 that extends perpendicularly up from base wall 16 at locations spaced outwardly from well array 30. Peripheral sidewall 40 includes a top edge 41 that defines a plane aligned substantially parallel to top surface 32 of well array 30. Top surface 32 of well array 30 is recessed relative to top edge 41 of peripheral sidewall 40 as shown most clearly in FIGS. 1, 2, 5 and 6. Peripheral sidewall 40 includes first and second end sections 42 and 44 respectively and first and second sidewall sections 46 and 48 respectively. End wall sections 42 and 44 and sidewall sections 46 and 48 are not linear. Rather, first end wall section 42 includes an indentation 43 disposed symmetrically thereon. Portions of first end wall section 42 defined by indentation 43 are spaced from first end 22 of peripheral skirt 20 by distance "a". In contrast, portions of end wall section 42 closer to sidewall sections 46 and 48 are spaced a distance "b" from first end edge 22. Distance "a" exceeds distance "b".

Second end wall section 44 of peripheral side wall 40 is substantially symmetrical with first end wall section 42. More particularly, second end wall section 44 includes a symmetrically disposed indentation 45. First and second sidewall sections 46 and 48 also are characterized by symmetrically disposed indentations 47 and 49 respectively.

First end wall section 42 meets first and second sidewall sections 46 and 48 at well defined right angle corners. However, second end wall section 44 meets sidewall sections 46 and 48 at truncated corners to provide a rotational orientation for well plate 12.

Multi-well tray 12 further includes first and second robotic gripper pads 56 and 58 that extend perpendicularly up from base wall 18 at locations aligned with first and second sides 26 and 28 of skirt 20. Robotic gripper pads 56 and 58 have top edges that lie in a plane parallel to the plane defined by top edge 41 of outer peripheral sidewall 40 of well plate 12, but disposed closer to base wall 16. Robotic gripper pads 56 and 58 also have outer surfaces 57 and 59 respectively that are parallel to one another.

Lid 14 is formed unitarily from a resin material, and preferably the same material as well plate 12. Lid 14 includes substantially planar central panel 60 and a peripheral frame 62. Peripheral frame 62 has a top wall 64 that is parallel to central panel 60 but offset upwardly from central panel 60. Peripheral frame 62 also includes a skirt 66 that depends down from top wall 64 for telescoping over peripheral sidewall 40 of well plate 12. Frame 62 is configured so that top wall 64 can rest on and closely engage top edge 41 of peripheral sidewall 40 of well plate 12 to control evaporation of liquid from well array 30. Additionally, skirt 66 extends from top wall 64 of frame 62 a distance less than the height of peripheral sidewall 40 of well plate 12. Thus, skirt 66 will not touch base wall 16 of well plate 12, and top wall 64 is assured of sealing against top edge 41 of peripheral side wall 40. In this embodiment, central panel 60 does not rest on top surface 32 of well array 30 to seal individual wells 34. However, other embodiments may have a lid configured to close each well 34. Skirt 66 includes first and second end walls 72 and 74 and first and second sidewalls 76 and 78. First and second end walls 72 and 74 are formed respectively with indentations 73 and 75 that nest with indentations 43 and 45 of peripheral sidewall 40 of well plate 12. Similarly, first and second sidewalls 76 and 78 are formed with indentations that nest respectively with indentations 47 and 49 of peripheral sidewall 40 of well plate 12. Indentations 73, 75, 77 and 79 are disposed at locations that will align with the solenoid pins of a robotic stacker so that plate assembly 10 can be dropped efficiently from the bottom of a stacked array without separating lid 14 from well plate 12.

Lid 14 further includes robotic gripper pads 86 and 88 that project from frame 62. More particularly, robotic gripper pads 86 and 88 extend down from the plane defined by top wall 64 of frame 62. Robotic gripper pads 86 and 88 have outer surfaces 87 and 89 that align respectively that with outer surfaces 57 and 59 of robotic gripper pads 56 and 58 on well plate 12. Additionally, robotic gripper pads 86 and 88 are dimensioned to be spaced slightly from the top edges of robotic gripper pads 52 and 54 when lid 14 rests on well plate 12. Outer surfaces 87 and 89 of robotic gripper pads 86 and 88 can be gripped by robotic grippers substantially simultaneously with outer surfaces 57 and 59 of robotic gripper pads 56 and 58 for lifting plate assembly 10 from the top of a stack of such plate assemblies.

The number of wells required for a well plate vary substantially based on the volume of liquid required for a particular laboratory test and in accordance with the specifications of the laboratory equipment. As noted above, the number of wells employed on well plates vary from 1 to 4,080 in accordance with certain established standards. Some well plates are manufactured by molding an appropriate well array and then mounting the molded well array to a base that has a uniform footprint. The mounting can be by purely mechanical means, such as a snap fit or by application of adhesive or ultrasonic welding. Other well plates are manufactured by dedicated mold pairs that unitarily mold a well plate of appropriate dimensions. The well plate 12 of the subject invention preferably is molded with a first mold defining a standard base wall 16 and a mating second mold defining a standard peripheral wall 40 of the well plate 12. Additionally, the mold assembly includes a plurality of mold inserts, any one of which can be mounted in the mating second mold for forming a well array 30 with an appropriate number of wells 34. Thus, post-molding assembly steps can be avoided and molding equipment can be adapted at low cost for producing plate assemblies 10 with a specified number of wells 34 with a substantially reduced cost, as compared to costs associated with dedicated molds.

Plate assembly 10 is employed by depositing liquid specimens into wells 34 of well array 30 by robotic equipment that employs an array of pipettes corresponding in number and location to wells 34. Lid 14 then is telescoped onto well plate 14. In this mounted condition, top wall 64 of frame 62 will rest on top edge 41 of peripheral end wall 40 of well plate 12 to substantially seal wells 34 to prevent or minimize evaporation. Indentations 73, 75, 77 and 79 of lid 14 will nest with indentation 43, 45, 47 and 49 of well array 30 and will be spaced inwardly from edges 22, 24, 26 and 28 of skirt 20 of well plate 12. Additionally, robotic gripper pads 86 and 88 of lid 14 will align with robotic gripper pads 56 and 58 of well plate 12. Outer surfaces 87 and 89 of robotic gripper pads 86 and 88 will align with outer surfaces 57 and 59 of robotic gripper pads 56 and 58 on well plate 12.

Plate assemblies 10 may be stacked in a laboratory for a selected time while biological samples in the respective wells 34 are permitted to grow or react. Plate assemblies 10 then can be removed sequentially from the bottom of a stacked array by actuation of solenoid pins of a robotic stacker. More particularly, the pins will align with the indentations 73, 75, 77 and/or 79. The pins will retract sufficiently to allow well plate assembly 10 to drop onto the elevator lift of the robotic stacker. The pins then will quickly extend to engage the next lowest well plate assembly 10. The indentations 73, 75, 77 and 79 ensure that the pins will engage the next sequential plate assembly 10 without separating lid 14 from its respective well plate 12. The ability to stack and process well plates 12 with lids 14 in position substantially reduces evaporation. Assemblies 10 also can be used with robotic grippers that function to engage robotic gripper pads 56, 58, 86 and 88 from opposed sides of assembly 10 for lifting and transporting assembly 10 to a location for analysis.

What is claimed is:

1. A plate assembly comprising:
a well plate having a substantially rectangular base wall with a top surface and an outer periphery, a well array extending up from said top surface of said base wall and disposed inwardly from said outer periphery of said base wall, said well array having at least one upwardly open well, a peripheral wall projecting up from said top surface of said base wall and extending around said well array, said peripheral wall including a pair of parallel sides extending between a pair of parallel ends, at least one robotic gripper pad being disposed along each said side spaced from said ends, wherein portions of said sides surrounding each said robotic gripper pad being spaced inwardly from said outer periphery of said base wall and spaced inwardly from said robotic gripper pads; and
a lid mounted on said well plate so as to overlie said well array and having a peripheral skirt telescoped over said peripheral wall of said well plate and over said robotic gripper pads, at least portions of said peripheral skirt of said lid being spaced inwardly from said outer periphery of said base wall, wherein said lid includes robotic gripper pads substantially registered with said robotic gripper pads of said well plate.

2. The assembly of claim 1, wherein each robotic gripper pad of said well plate is substantially coplanar with one of said robotic gripper pads of said lid.

3. The assembly of claim 1, wherein said at least one well comprises a plurality of wells.

4. The assembly of claim 1, wherein at least portions of the top surface of the base wall between said outer periphery of said base wall and said peripheral wall define a plane, said well array having a top surface defining a plane substantially parallel to said plane of said top surface of said base wall.

5. The assembly of claim 4, wherein said peripheral wall of said well plate includes a top edge substantially parallel to said top surface of said well array.

6. The assembly of claim 1, wherein said ends having portions spaced inwardly from said outer periphery of said base wall.

7. The assembly of claim 1, wherein said lid includes a top wall adjacent said peripheral skirt, said top wall being engaged with top edges of said peripheral wall of said well plate for substantially sealing said well array and limiting evaporation.

8. The plate assembly of claim 1, wherein said peripheral skirt of said lid is spaced from said base wall of said well plate.

9. The plate assembly of claim 1, wherein said well array and said peripheral wall are molded unitarily with said base wall of said well plate.

10. A plate assembly comprising:
a well plate having a substantially rectangular base wall with an outer periphery, said outer periphery including first and second substantially parallel sides and first and second substantially parallel ends extending between said parallel sides, a well array formed on said base wall inwardly from said outer periphery, said well array including a top surface and at least one well extending into said top surface, a peripheral wall extending up from said base wall at locations between said well array and said outer periphery, said peripheral wall including indentations spaced inwardly of said outer periphery of said base wall, at least two opposed robotic gripper pads extending up from said base wall at locations substantially registered with said outer periphery; and
a lid mounted to said peripheral wall of said well plate so as to overlie said well array, said lid including a peripheral skirt nested with at least portions of said peripheral wall of said well plate said peripheral skirt of said lid including indentations nested with said indentations of said peripheral wall of said well plate and spaced inwardly from said outer periphery of said base wall of said well plate, said lid further including at least two opposed robotic gripper pads substantially aligned with, and positioned to telescope over, said robotic gripper pads of said well plate.

11. The plate assembly of claim 10, wherein said robotic gripper pads of said well plate and of said lid are substantially registered with said sides of said outer periphery of said well plate.

12. The plate assembly of claim 10, wherein said indentations include indentations in said peripheral wall of said well plate and in said peripheral skirt of said lid such that said robotic gripper pads each are between a pair of said indentations.

13. The plate assembly of claim 12, wherein the robotic gripper pads of said well plate are spaced from said robotic gripper pads of said lid a sufficient distance to ensure that said lid is seated securely on said top edge of said peripheral wall of said well plate.

14. The plate assembly of claim 13, wherein said skirt of said lid is spaced from said base wall of said well plate to ensure that said lid is seated securely on said top edge of said peripheral wall of said well plate.

15. The plate assembly of claim 10, wherein said peripheral wall and said well array are molded unitarily with said base wall.

16. The assembly of claim 1, wherein outer surfaces of said robotic gripper pads are substantially registered with said outer periphery of said base wall.

* * * * *

UNITED STATES PATENT AND TRADEMARK OFFICE
CERTIFICATE OF CORRECTION

| | | |
|---|---|---|
| PATENT NO. | : 7,666,362 B2 | Page 1 of 1 |
| APPLICATION NO. | : 10/943687 | |
| DATED | : February 23, 2010 | |
| INVENTOR(S) | : Michael S. Shanler | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1511 days.

Signed and Sealed this

Twenty-eighth Day of December, 2010

David J. Kappos
*Director of the United States Patent and Trademark Office*